Figure 1:
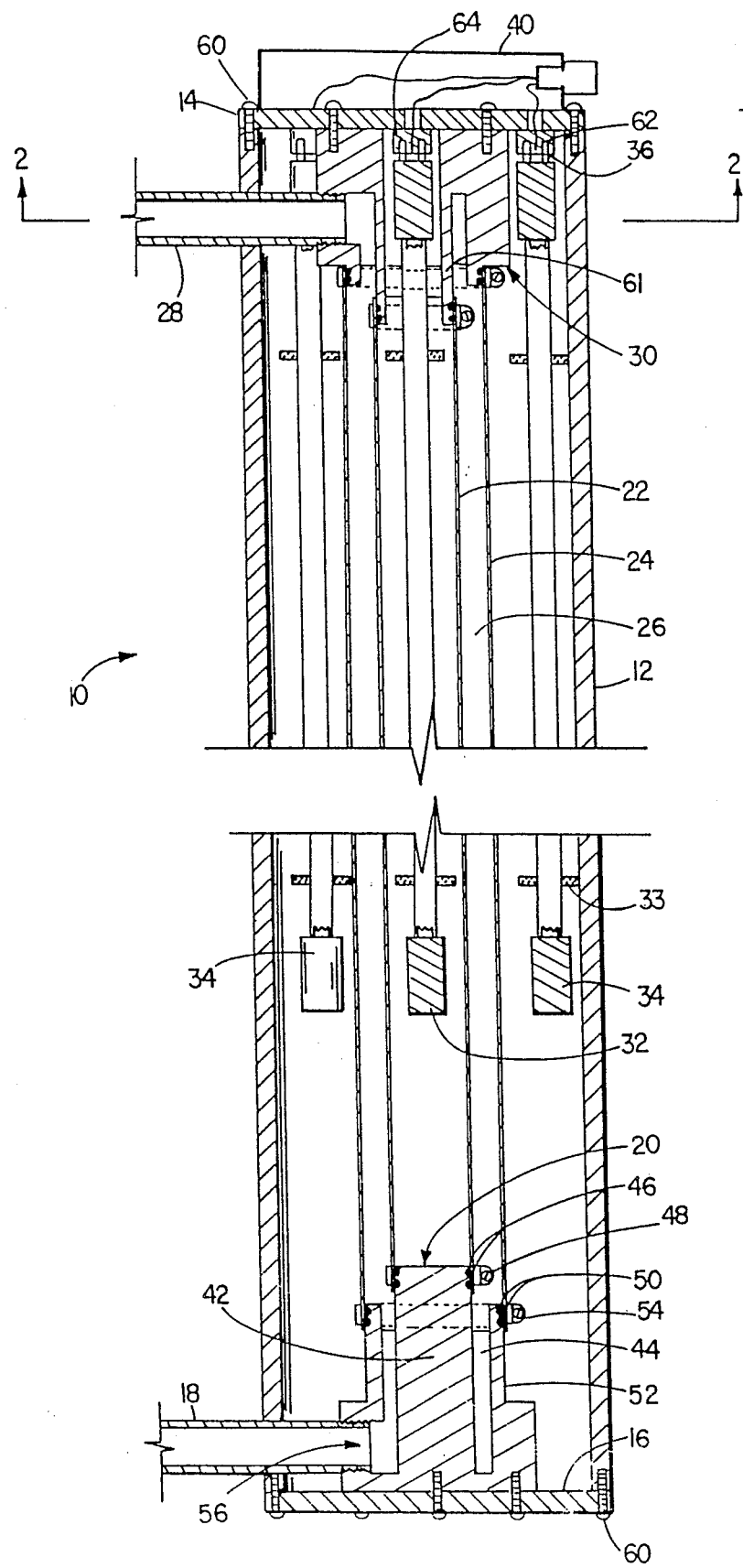

United States Patent [19]

Jhawar et al.

[11] Patent Number: 4,968,891

[45] Date of Patent: Nov. 6, 1990

[54] DISINFECTING A FLUID WITH ULTRAVIOLET RADIATION

[76] Inventors: Makhan M. Jhawar, 1018 Oldham Way, Encinitas, Calif. 92024; Eugene N. Short, Elwyn Rd., Portsmouth, N.H. 03801

[21] Appl. No.: 441,008

[22] Filed: Nov. 22, 1989

[51] Int. Cl.$^5$ .............................................. A61L 2/10
[52] U.S. Cl. .................................. 250/438; 250/436; 422/24
[58] Field of Search ........... 250/436, 438, 435, 432 R; 422/24; 210/748

[56] References Cited

U.S. PATENT DOCUMENTS

| | | | |
|---|---|---|---|
| 2,147,857 | 2/1939 | O'Brien | 422/24 |
| 2,340,890 | 2/1944 | Lang et al. | 250/48 |
| 3,527,940 | 9/1970 | Balanca et al. | 250/44 |
| 3,634,025 | 1/1972 | Landry | 21/102 |
| 3,700,406 | 10/1972 | Landry | 21/54 |
| 3,767,918 | 10/1973 | Graybeal | 250/433 |
| 3,837,800 | 9/1974 | Wood | 21/54 |
| 3,889,123 | 6/1975 | Bosshard | 250/437 |
| 3,894,236 | 7/1975 | Hazelrigg | 250/435 |
| 4,471,225 | 9/1984 | Hillman | 250/436 |
| 4,602,162 | 7/1986 | Sperry, III et al. | 250/436 |
| 4,694,179 | 9/1987 | Lew et al. | 250/431 |
| 4,766,321 | 8/1988 | Lew et al. | 250/431 |
| 4,798,702 | 1/1989 | Tucker | 422/24 |
| 4,904,874 | 2/1990 | Ellner | 250/432 R |

FOREIGN PATENT DOCUMENTS 2450612  11/1980  France .................................. 422/24

*Primary Examiner*—Jack I. Berman
*Attorney, Agent, or Firm*—Fish & Richardson

[57] ABSTRACT

A process of exposing a fluid medium, such as machine oil, to radiant energy and a device to carry out that process include providing at least two juxtaposed, elongated radiant energy source, such as ultraviolet germicidal radiation sources, providing a passage between the sources that is typically less than an inch thick and that has walls capable of transmitting the radiant energy, providing for fluid flow in a direction substantially parallel to the radiant energy sources, passing a fluid medium in a thin film through the passage, and simultaneously exposing the fluid medium to the radiant energy by irradiating the fluid medium with the radiant energy sources. Preferably, the passage is in the configuration of an annulus surrounding one of the radiant energy sources, and a plurality of radiant energy sources is arrayed around the passage.

11 Claims, 2 Drawing Sheets

DISINFECTING A FLUID WITH ULTRAVIOLET RADIATION

BACKGROUND OF THE INVENTION

This invention relates to radiant energy processing and to a process for exposing a fluid medium to radiant energy, such as ultraviolet radiation.

Ultraviolet radiation is lethal to microorganisims in fluids in practically attainable dosages. In existing ultraviolet disinfecting devices, the fluid to be sterilized is transported in quartz or Teflon TM pipes in coaxial arrangement around an ultraviolet germicidal lamp or in a helical or serpentine path around or between banks of ultraviolet lamps. The fluid is irradiated through the transparent walls of the pipes.

SUMMARY OF THE INVENTION

In general, the invention features a process of exposing a fluid medium to radiant energy and a device to carry out that process that includes providing at least two juxtaposed, elongated radiant energy sources, such as ultraviolet germicidal radiation sources, providing a passage between the sources that is typically less than an inch thick (preferably less than one-half inch thick) and that has walls capable of transmitting the radiant energy, providing for fluid flow in a direction substantially parallel to the radiant energy sources, passing a fluid medium in a thin film through the passage, and simultaneously exposing the fluid medium to the radiant energy by irradiating the fluid medium with the radiant energy sources.

In preferred embodiments, an outlet end of the passage is spaced from an inlet end, preferably higher than the inlet end and most preferably in substantially vertical alignment with the inlet end, and the direction of fluid flow between the inlet and the outlet is transverse to the cross-sectional area of the passage. The passage is preferably substantially in the configuration of an annulus surrounding one of the radiant energy sources, and preferably a plurality of radiant energy sources is arrayed around the passage.

In another embodiment, radiant energy sources are arranged in two parallel banks on either side of the passage for fluid flow.

The radiant energy processing device of the invention is easy to assemble and inexpensive to build and operate. A desirable level of processing of the fluid is accomplished at a rapid rate as the invention maximizes surface area exposure per unit distance traveled by the fluid. The invention takes advantage of the natural turbulence of fluids near a surface without baffles or turbulence promoters.

Figure 2:
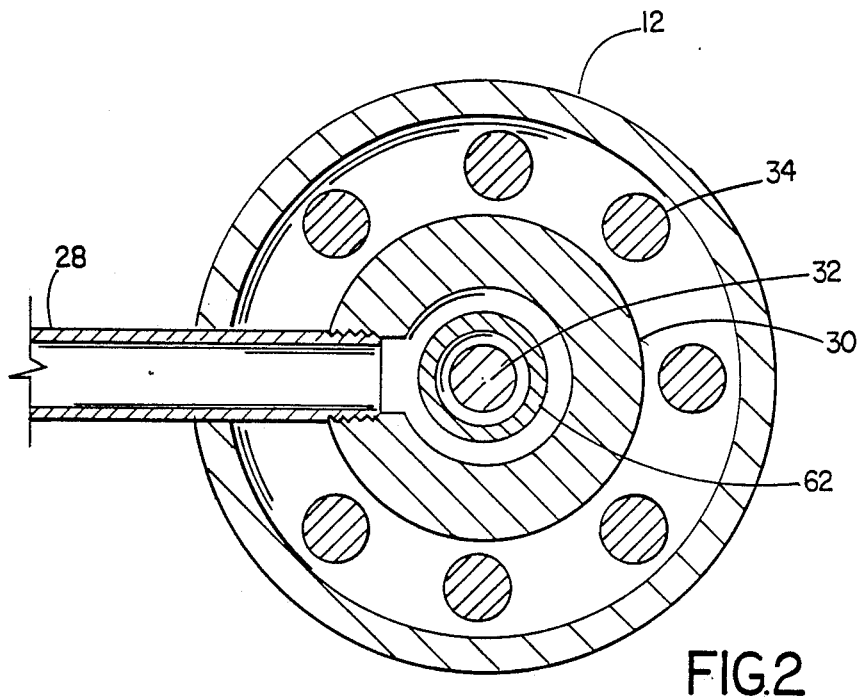

Other features and advantages of the invention will be apparent from the following detailed description and from the claims when read in connection with the accompanying drawings in which:

FIG. 1 is a longitudinal section through the center axis of an ultraviolet disinfecting device according to the invention; and FIG. 2 is a transverse section through an ultraviolet disinfecting device according to the invention through section 2—2 of FIG. 1.

Referring to FIG. 1 for an overview, an ultraviolet disinfecting device 10 is made of a polished or anodized large aluminum pipe 12 with covers 14, 16 on both ends. The fluid medium or the liquid to be disinfected enters the device through an inlet pipe 18 and travels into the bottom header block 20 which has attached two ultraviolet transparent Teflon TM tubes 22, 24. The fluid flows upwards in the thin annular passage (annulus) 26 created between the Teflon TM tubes 22, 24 and exits through outlet pipe 28 in the top header block 30. Ultraviolet lamps 32, 34 with connecting pins 36 on only one end are suspended in the chamber of device 10 from top cover 14; one ultraviolet lamp is placed inside inner Teflon TM tube 22 while a multiple number of ultraviolet lamps 34 are arranged on the outside of the outer Teflon TM tube 24, thus providing radiant energy from both sides of annulus 26. Ceramic centering rings 33 are placed at intervals along the ultraviolet lamps 32, 34. An electrical connection box 40 is attached to top cover 14 while the ballasts (not shown) required for energizing the lamps are mounted in a separate fan cooled enclosure.

Referring to FIGS. 1 and 2, the bottom header 20, made of an aluminum or stainless steel block, is typically 2.50" in diameter, with a solid central shaft portion 42, 1.00" in diameter and 3.00" high, 0.50" longer than the rest of the block. Around the central shaft is a 0.2" wide channel 44 which extends to within 0.25" of the bottom of header 20. Two O-rings 46 are mounted in grooves on the end of shaft 42, and inner Teflon TM tube 22 is slipped over the O-rings and held in place by stainless steel hose clamp 48. Outer Teflon TM tube 24 is slipped over O-rings 50 in grooves on the outside of the main bottom header portion 52 and secured in place with hose clamp 54. Inner and outer Teflon TM tubes 22, 24 create between them annular passage 26 which is 0.40" thick. A 0.75" diameter inlet 56 provides access to channel 44 in the header block and is threaded to accept inlet pipe 18.

The outlet or the top header 30 is also made of a polished aluminum or stainless steel block. Unlike the bottom header, the top header central shaft 61 is hollow, which allows for the insertion of ultraviolet lamp 32. The inner and outer Teflon TM tubes 22, 24 are attached to the central shaft and the main portion of the top header in the same manner as they are to the bottom header.

The top and bottom header blocks 30, 20 are positioned in the center of their respective end covers 14, 16 and attached by screws 60. Inside of the top cover 14, lamp holders 62 are attached by screws at precise locations in such a manner that attached lamps 34 surround outer Teflon TM tube 24, typically at 22½°, 45°, 90° or 180° intervals. Lamp holder 64, in the middle of the top cover, receives ultraviolet lamp 32 which is suspended in the center of inner Teflon TM tube 22. The whole top cover assembly, with attached ultraviolet lamps, is removable for lamp replacement.

When the ultraviolet disinfecting device 10 is in operation, fluid flowing into inlet pipe 18 empties into channel 44 and is forced upward past the edge of bottom header portion 52 and into annular passage 26 between Teflon TM tubes 22, 24. The natural turbulence within annular passage 26 constantly churns the thin film of fluid, throwing fluid particles on the walls of the Teflon TM tubes The energized outer ultraviolet lamps 34 irradiate the fluid in annular passage 26 from the outside-in, while the ultraviolet lamp 32 inside the inner Teflon TM tube irradiates the fluid from the inside-out. As the fluid travels from the bottom of the unit to the top, it is disinfected and exits from the top exit pipe 28.

Other embodiments are within the claims. For example, instead of the coaxial arrangement described, two parallel banks of elongated ultraviolet lamps can be arranged to provide between them, in a sandwich arrangement, a thin passage for flow of the fluid to be disinfected. Several disinfecting devices can be arranged in series for additional purification. A wide variety of fluids, from clear ones such as water to turbid or opaque ones such as milk, beer, wine or other beverages, or emulsified oil for machine lubrication, can be disinfected in the device of the invention. The invention may be used for other radiant energy or photochemical reactions.

What is claimed is:

1. A process of exposing a fluid medium to radiant energy from at least two juxtaposed, elongated radiant energy sources adjacent to respective walls capable of transmitting said radiant energy comprising the steps of
    defining a passage between said radiant energy sources having an inlet spaced from an outlet and generally parallel to said sources,
    passing said fluid medium in a thin film through said passage in a direction generally parallel to said sources, and
    simultaneously exposing the fluid medium to said radiant energy through said walls.

2. The process of claim 1 further comprising passing said fluid first throuqh said inlet, and then through said outlet after exposure to said radiant energy.

3. The process of claim 1 further comprising confining said fluid medium to annular flow around one of said sources.

4. A device for exposing a fluid medium to radiant energy, said device comprising
    at least two juxtaposed, elongated radiant energy sources, and
    walls defining a narrow passage between said sources, said passage having an inlet and outlet,
    said walls being capable of transmitting said radiant energy,
    said passage providing for thin film fluid flow in a direction substantially parallel to said radiant energy sources between said inlet and said outlet.

5. The device of claim 4 wherein said direction provided for fluid flow is transverse to the cross-sectional area of said passage.

6. The device of claim 4 wherein the outlet from said passage is higher than the inlet to said passage.

7. The device of claim 6 wherein the outlet from said passage is in substantially vertical alignment with the inlet to said passage.

8. The device of claim 4 wherein said passage is substantially in the configuration of an annulus surrounding one of said radiant energy sources 9. The device of claim 8 further comprising a plurality of said radiant energy sources in annular arrangement around said passage.

10. The device of claim 4 comprising a plurality of said radiant energy sources arranged in two parallel banks on either side of said passage.

11. The device of claim 4 wherein said radiant energy sources comprises germicidal ultraviolet radiant energy sources.

* * * * *

UNITED STATES PATENT AND TRADEMARK OFFICE
CERTIFICATE OF CORRECTION

PATENT NO. : 4,968,891

DATED : November 6, 1990

INVENTOR(S) : Makhan M. Jhawar et al.

It is certified that error appears in the above-identified patent and that said Letters Patent is hereby corrected as shown below:

Column 2, line 62, after "tubes" should appear --.--.

Column 3, line 28, "throuqh" should read --through--.

Signed and Sealed this

Thirteenth Day of October, 1992

Attest:

DOUGLAS B. COMER

Attesting Officer        Acting Commissioner of Patents and Trademarks